United States Patent [19]

Solano et al.

[11] Patent Number: 4,921,478
[45] Date of Patent: May 1, 1990

[54] CEREBRAL BALLOON ANGIOPLASTY SYSTEM

[75] Inventors: Scott J. Solano, Lowell, Mass.; Myles L. Saunders, Beverly Hills, Calif.; James Crittenden, Hollis, N.H.

[73] Assignee: C. R. Bard, Inc., Murray Hill, N.J.

[21] Appl. No.: 159,539

[22] Filed: Feb. 23, 1988

[51] Int. Cl.⁵ .......................................... A61M 25/02
[52] U.S. Cl. ........................................ 604/53; 604/96
[58] Field of Search ............... 128/328, 344, 348.1; 604/53, 96–103, 256

[56] References Cited

U.S. PATENT DOCUMENTS

| | | | |
|---|---|---|---|
| 3,833,004 | 9/1974 | Vazquez et al. | 604/100 |
| 4,024,873 | 5/1977 | Antoshkiw et al. | 604/96 |
| 4,148,319 | 4/1979 | Kasper et al. | 604/96 |
| 4,423,725 | 1/1984 | Baran et al. | 604/101 |
| 4,655,746 | 4/1987 | Daniels et al. | 604/101 X |

FOREIGN PATENT DOCUMENTS

| | | | |
|---|---|---|---|
| 457471 | 3/1975 | U.S.S.R. | 128/328 |
| 929111 | 5/1982 | U.S.S.R. | 604/101 |

*Primary Examiner*—Dalton L. Truluck

[57] ABSTRACT

An occlusion catheter for use during the therapeutic intervention of a cerebral blood vessel for flushing away fluid and debris from the area of the therapeutic intervention is provided. The catheter carries an inflatable occlusion balloon capable of being formed into a funnel with the larger end of the funnel facing distally. The funnel-shaped occlusion balloon seals the walls of the vessel to establish retrograde flow of blood. The peripheral walls of the funnel meet the vessel walls at an oblique angle and channel fluid and debris flowing proximally into the funnel to efflux ports at the base of the funnel.

45 Claims, 8 Drawing Sheets

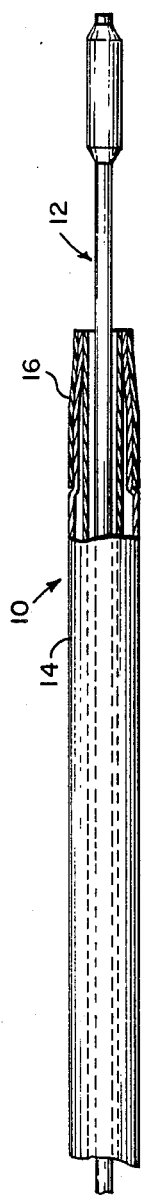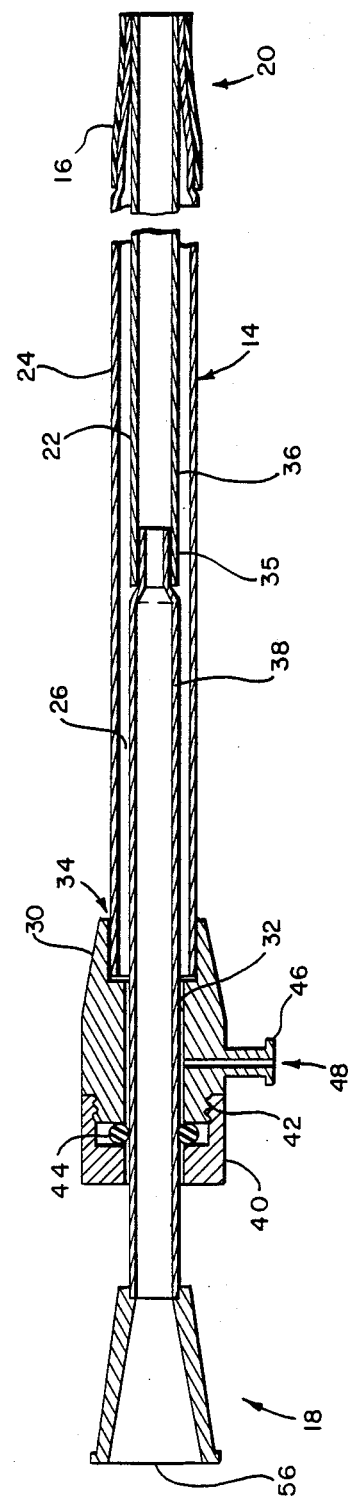

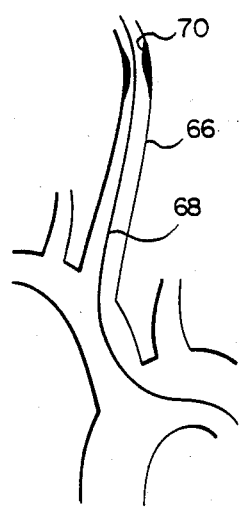
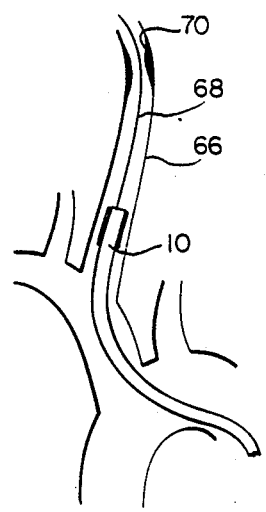
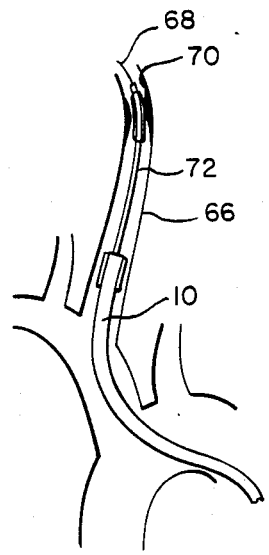
Fig. 9A    Fig. 9B    Fig. 9C
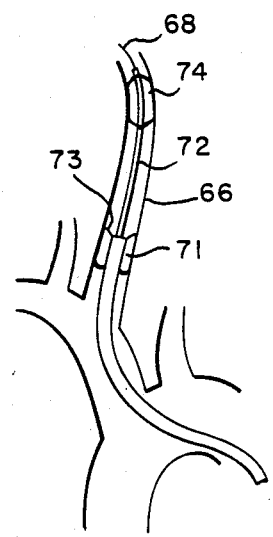
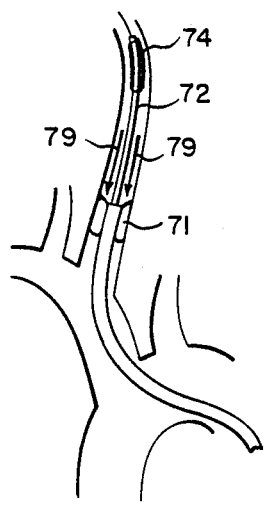
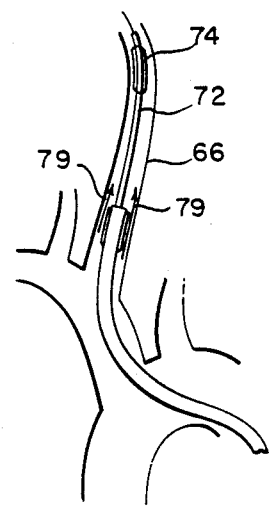
Fig. 9D    Fig. 9E    Fig. 9F

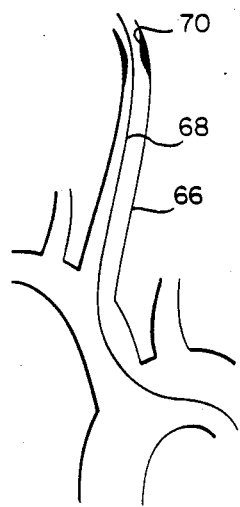 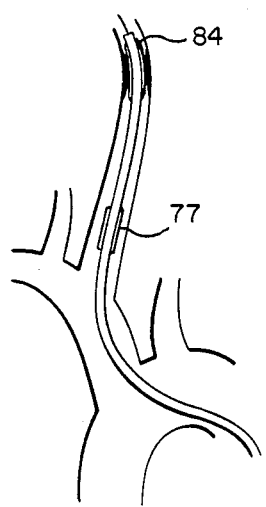 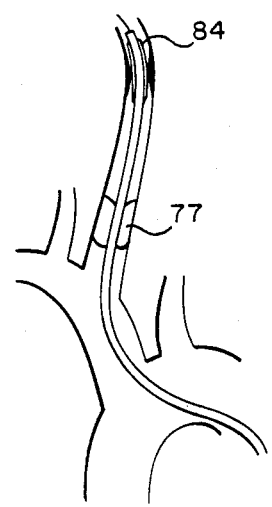
Fig. 11A          Fig. 11B          Fig. 11C
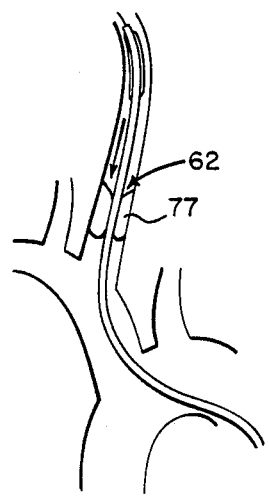 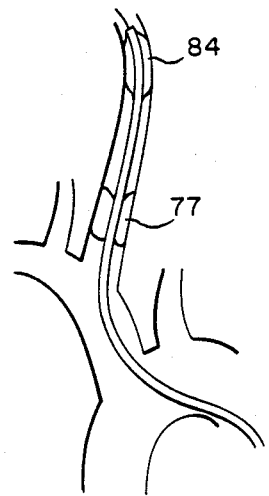
Fig. 11E          Fig. 11D

CEREBRAL BALLOON ANGIOPLASTY SYSTEM

This invention relates to an angioplasty system for treating cerebral arteries.

BACKGROUND OF THE INVENTION

A stenosed blood vessel can be life threatening and often requires therapeutic intervention. Nonsurgical intervention procedures have been used with increasing regularity in recent years as a treatment for stenosed arteries. Examples of nonsurgical intervention include treatments such as balloon angioplasty, mechanical removal, laser fiber-optical treatment and localized chemical treatment.

These procedures typically involve the percutaneous introduction of the treatment device into the lumen of the artery, via a catheter. For example, balloon angioplasty involves the use of a special catheter having a balloon at its distal end. The catheter is inserted percutaneously into the patient's arterial system and is advanced and manipulated to place the balloon within the stenosis in the artery. The balloon then is inflated under substantial pressure to press the plaque and plaque-laden arterial wall radially outwardly to enlarge the stenosed region of the artery. When successful, the procedure may avoid the necessity for major surgery.

Treating cerebral arteries poses unusual risks The above listed forms of non-surgical treatment potentially involve the release of debris into the circulation as the plaque is manipulated by balloon angioplasty, mechanical removal laser, fiber optical treatment and localized chemical treatment. The debris can then be carried distally by the circulating blood to the vessels of the brain where they can occlude cerebral vessels resulting in a stroke, having potentially devastating effects. Although cerebral percutaneous transluminal angioplasty has been clinically performed, previous experience has been limited to a small number of dilitations of proximal, extra-cranial vessels, and rare cases of distal intra cranial vessels with commercially available dilatation balloons. Fear of causing embolic strokes has thus far prevented the wide spread use of balloon angioplasty in the cerebral vascular system.

SUMMARY OF THE INVENTION

The present invention permits treatment of the proximal extra-cranial and distal intra cranial cerebral vessels while eliminating/reducing the risk of embolic stroke by removing the debris from the circulation before it travels distally. An occlusion device of special design is placed in a cerebral artery proximal to the treatment site. The device is used to briefly occlude the circulating blood flow in the artery at the time the obstructive lesion is manipulated. Passages within the cerebral circulation cause blood to flow retrograde towards the occlusion device, flushing the debris out of the body through a lumen in the device.

The cerebral circulation system generally may be seen as divided into two sets of contralateral arteries, one set feeding the left side of the brain and the other feeding the right side. A large number of major communicating vessels connects these contralateral arteries. As such, if pressure becomes low enough on a given side, the physiological pressure on the contralateral side is sufficient to cause blood to flow across the communicating vessels and in a retrograde fashion towards the low pressure source. According to the invention, by temporarily occluding the natural antegrade flow in a cerebral vessel, and by providing a low, atmospheric pressure outlet for the blood, this retrograde effect can be artificially induced. If the temporary occlusion is placed proximal to a treatment site, the resulting retrograde flow can be used to flush post treatment debris safely away from the brain and out of the body.

The catheter system for achieving retrograde flow and treatment employs two components, an intervention component, such as a conventional dilitation balloon, and an occlusion component. The occlusion component has the ability to assume a funnel shape with the larger end facing distally and with the periphery of the larger end contacting the walls of the vessel. The occlusion component effects a circumferential seal against the vessel lumen which promotes retrograde flow of blood toward the apex of the funnel into efflux ports located at the apex or base. The circumferential seal must be adequate to prevent leakage or entrapment of debris at the funnel vessel wall interface as blood and debris are channeled into the funnel to the efflux ports. The efflux ports are located at the base of the funnel to ensure that debris is not entrapped, but rather is collected and removed from the vessel. The intervention component and the occlusion component may be mounted together on a single catheter or separately on two coaxial catheters.

Preferably, an elongated shaft is introduced into the blood vessel lumen. The shaft has an inflatable component secured at or near its distal end, the distal end of inflatable component being capable of forming a funnel with the larger end of the funnel facing distally on the shaft when inflated. An inflation lumen passes axially through the shaft and communicates with the interior of the inflatable component and enables the inflatable component to be inflated to form a seal against the vessel lumen. Efflux ports at the apex of the funnel communicate with an efflux lumen that passes axially through the shaft, enabling fluid and debris which enters the funnel to be carried through the shaft toward its proximal end. Because the inflatable occlusion component must produce a critical circumferential seal with the surrounding vessel in order to assure retrograde flow, it is preferably elastic in nature. Although a non elastic balloon, such as those made from thin-walled thermoplastic material, can be pre-molded with a funnel shape at their distal end, then cannot assure an adequate circumferential seal unless precise matching of the vessel and balloon size is accomplished. This is generally not possible in a typical fluoroscopic procedure. An elastic balloon will provide an adequate seal, but will not assume any shape other than semi-spherical without the aid of an additional means of forcing it into the desired funnel shape, hereafter called a forming element.

Preferably, the elongated shaft is composed of coaxial inner and outer shafts connected at their distal ends, and the forming element is a plurality of axial struts on the outer shaft. The inner shaft extends axially and movably within the outer shaft and is connected to the distal end of the struts for moving the distal and proximal ends of the struts closer to one another and for moving the intermediate portions of the struts radially outwardly toward the wall of the vessel lumen to form a funnel shape. The struts act on the distal end of an overlying inflated balloon to form the balloon into the desired funnel shape.

Alternately, the inflatable component is a balloon with a discrete forming element within the balloon. The forming element may be a cylinder, with one end slit axially and splayed over a conical mold to produce a funnel shape. The remaining cylindrical portion is bonded to the shaft. The balloon is bonded over the forming element, with the proximal end bonded to the shaft proximally of the forming element and the distal end of the balloon bonded to the shaft under the distal end of the splayed portion of the forming element. Inflation of the balloon then causes the forming element to assume its funnel shape, thus forcing the balloon into the desired configuration upon inflation.

Preferably, the occlusion component and the intervention component are separate elements. The occlusion component may be a balloon and a forming element carried on an elongated shaft. The intervention component may be a dilitation balloon carried on a separate balloon dilitation catheter. The dilitation balloon and catheter may be delivered to the stenosis through a lumen extending axially through the elongated shaft of the occluson component. According to this construction, the dilitation balloon may be placed independently of the occlusion balloon.

According to the method of the invention, the occlusion component is introduced into the cerebral artery to a location just proximal of the stenosis. The occlusion component then is inflated into its funnel shape to occlude the flow of blood in the vessel. Subsequently, the dilitation balloon is introduced through the occlusion device into the stenosis and inflated according to standard treatment procedures. Then the dilitation balloon is deflated and blood and debris are allowed to flow retrograde through the efflux ports at the apex of the funnel to remove all debris caused by the dilitation from the vessel. The inflation, deflation and debris removal steps may be repeated as required. Once the debris is removed, the occlusion component is deflated permitting regular antegrade blood flow. The device then may be removed.

It is an object of the invention to reduce the risk of microembolic cereberal vessel occlusion when treating a stenosed cerebral artery.

Another object of the invention is to occlude a cerebral artery in a manner to permit retrograde flow of blood and prevent the trapping of debris at the interface between the occlusion device and the vessel walls.

Another object of the invention is to provide a device capable of occluding a cerebral artery in a manner to permit the collection and removal of debris associated with treating a stenosis distal to the induced occlusion.

Another object of the invention is to provide a cerebral angioplasty system with components for occluding the cerebral artery at a location proximal to the site of the stenosis and for treating the stenosis while the vessel is occluded.

Still another object of the invention is to provide an occluding element for a catheter capable of assuming a funnel shape upon inflation with the larger end of the funnel facing distally.

BRIEF DESCRIPTION OF THE DRAWINGS

FIG. 1 illustrates the preferred embodiment of the angioplasty system of the present invention;

FIG. 2 is a cross section of the preferred embodiment of the occlusion component forming part of the system of FIG. 1;

FIGS. 9A-9F illustrate the preferred method of this invention using the angioplasty system shown in FIGS. 1-8;

FIGS. 11A-11E illustrate another method of the present invention using the system of FIG. 10.

DETAILED DESCRIPTION OF THE DRAWINGS

Figure 3:
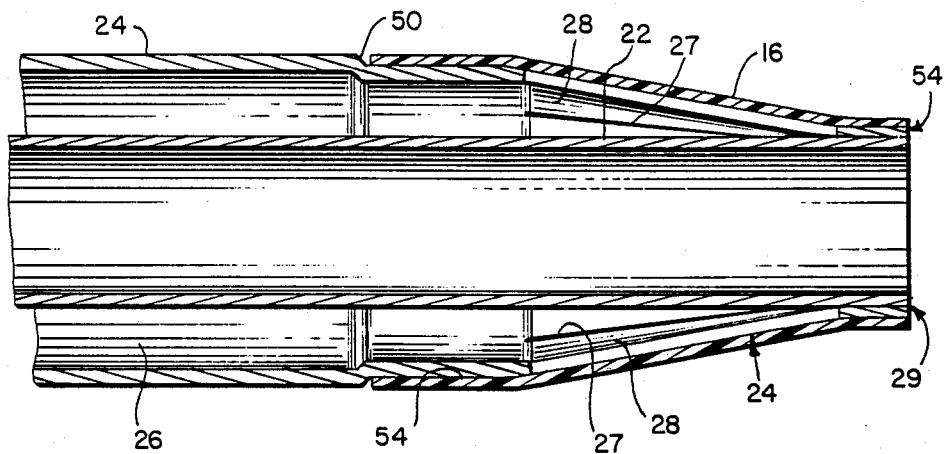
FIG. 3 is an enlarged view of the distal end of the occlusion component sown in FIG. 2.

The preferred embodiment of angioplasty system of this invention has separate occlusion and intervention components 10 and 12, respectively, as shown in FIG. 1. The occlusion component 10 includes an elongated shaft 14 sized to be introduced into a blood vessel. An inflatable occlusion balloon 16 is carried on the distal end of the elongated shaft 14. The occlusion balloon 16 is capable of being formed into a funnel shape with the larger end of the funnel facing distally. The elongated shaft 14 has a lumen through which the intervention component 12, preferably a conventional dilitation balloon catheter, may be introduced into the blood vessel. In this arrangement the dilitation balloon catheter is movable axially within the lumen of the elongated shaft 14.

The preferred embodiment of the occlusion component 10 is shown in some detail in FIG. 2. The elongated shaft 14 has a proximal end 18 and a distal end 20, the distal end 20 being that which is introduced into the patient and which carries the occluding device. The occluding device includes a balloon capable of forming a distally facing funnel in the blood vessel.

The elongated shaft 14 is composed of coaxial inner and outer shafts 22 and 24, respectively, operatively connected together at or near their distal ends. The annular space between the shafts defines an inflation lumen 26 which communicates with the interior of the inflatable occluding balloon 16 attached at the distal end of shaft 14.

The proximal end of shaft 14 is constructed to seal the proximal end of inflation lumen 26 while permitting axial movement of the inner shaft 22 within the outer shaft 24. To accomplish this, a T-body 30 having a lumen 32 is bonded to the proximal end of the outer shaft 24 such that the T-body lumen 32 is continuous with and axially extends the lumen of the outer shaft 24. The T-body lumen 32 is enlarged at its distal end as shown at 34 and receives the outer shaft 24 which is bonded in place.

The inner shaft 22 has a flexible portion and a rigid portion. The flexible portion 36 extends from the distal end 20 and terminates within the outer shaft 24 distally of the T-body 30, where the flexible portion 36 is attached to a rigid tubular member 38 which comprises the rigid portion. Thus, the inner lumen of the inner shaft 22 is continuous from end to end and consists of the lumen of the flexible portion and the lumen of the rigid tubular member. The rigid tubular member 38 preferably is made of stainless steel and may be a section of hypodermic tubing.

The rigid tubular member 38 extends beyond the proximal end of the outer shaft 24 and completely through the T-body lumen 32, terminating at a distance proximal to the T-body 30 sufficient to allow the rigid tubular member to be gripped in the operator's hand. The annular space between the rigid tubular member 38 and the walls of the T-body defining the T-body lumen 32 is continuous with the annular space between the coaxial inner and outer shafts.

A threaded cap 40 screws onto the threaded proximal end 42 of the T-body 30. The threaded cap 40 and the T-body 30 together define an annular channel at the proximal end of the T-body lumen 32 for capturing an annular elastomeric gasket 44. As the threaded cap 40 is screwed onto the T-body 30, the gasket 44 is compressed radially inwardly against the rigid tubular member 38 and against the proximal walls of the T-body 30 to seal the proximal end of the inflation lumen 26. Appropriate tightening of the gasket arrangement allows for the axial movement of the inner shaft 22 while maintaining the sealing of the inflation lumen 26.

The T-body 30 further is provided with luer-locking connector 46 through which a passage 48 communicates with the T-body lumen 32. This passage 48 allows fluid or gas under pressure to be introduced to and withdrawn from the inflation lumen 26 for inflating and deflating the balloon 16.

Figure 4:
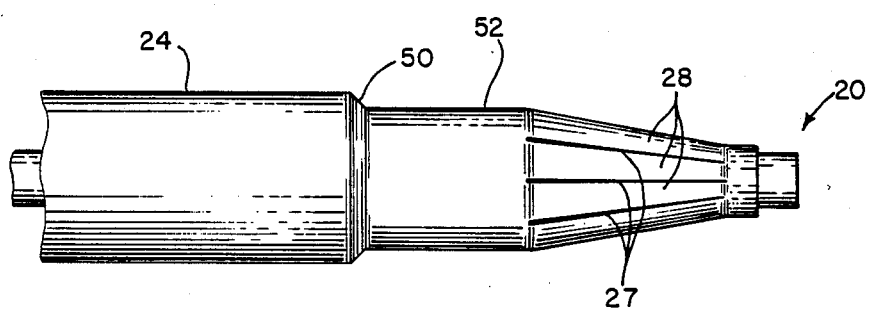
FIG. 4 is an enlarged side view of the distal end of the outer shaft of the occlusion component with the balloon removed.

The unique configuration of the distal end 20 of the elongated shaft 14 allows the formation of the funnel shaped occluding element. As shown in FIGS. 3 and 4, the inner shaft 22 has a uniform diameter at its distal end. The outer shaft's distal end is slit axially for about 18 mm as shown at 27, and the terminal 2 mm of this slit distal end is heat bonded to the distal end of the inner shaft 22. The heat bonding melts the distal ends of the inner and outer shafts together, eliminating the slits at this heat bonded area. The unmelted portion of the slits 27 define a cylindrical series of struts 28 at the distal end of the outer shaft. The outer shaft 24 at the region of the struts assumes a frustoconical shape decreasing in diameter in the distal direction to the heat bond 29. The inflatable balloon 16 is bonded to the outer shaft 24 such that it spans the strutted region of the outer shaft. The manner of attaching the balloon is discussed in greater detail below.

Figure 5A:
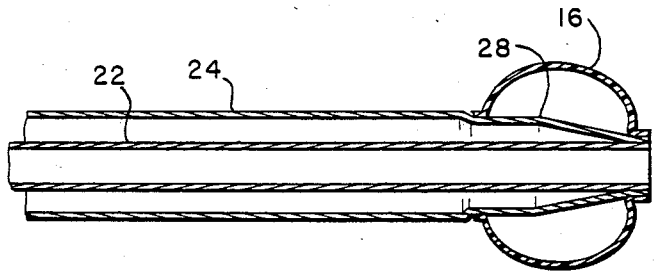
FIGS. 5A-5C are cross sectional views illustrating the manner in which the forming element of FIGS. 2 and 3 assumes a funnel shape.
Figure 5B:
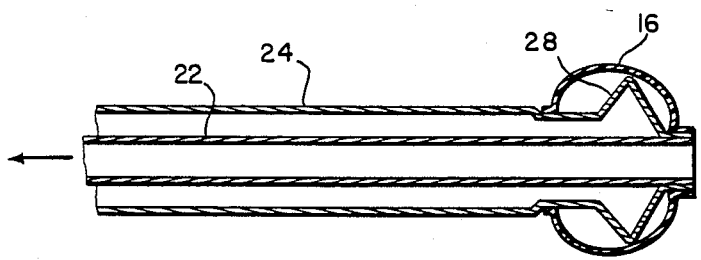
Figure 5C:
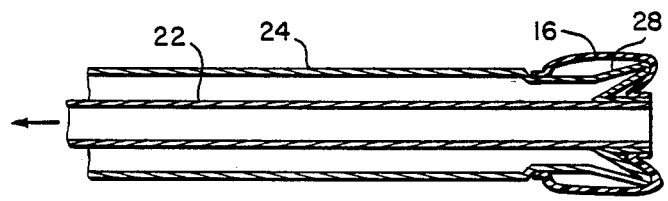

The operation of the occlusion component 10 to form the funnel shaped occluding element is illustrated in FIGS. 5A–5C. First, the inflatable balloon 16 is inflated as shown in FIG. 5A. Then the inner shaft 22 is displaced proximally (arrows) while holding the outer shaft 24 fixed, as suggested in FIG. 5B. This results in a radial buckling or folding deformation of the struts 28 in an outward direction as illustrated. As the inner shaft 22 continues to advance proximally, the struts contact the inner surface of the inflated balloon 16 and, being of a relatively stronger construction than the elastic material, begin to deform the balloon 16. Ultimately, the struts fold tightly upon themselves, with the struts forming the balloon 16 into the desired funnel shape (see FIG. 5C).

It should be understood that the selection of the material used for the outer shaft and the balloon is important to the proper operation of this embodiment of the occlusal component 10. If the material of the outer shaft is too stiff, or if the shaft walls are too thick, the struts will not deflect in the appropriate manner. Moreover, the entire device will be too stiff for insertion into the cerebral vasculature. On the other hand, if the material of the outer shaft is too thin or weak, then the struts will be too weak to form the elastic balloon into the appropriate funnel shape. Likewise, the properties of the balloon are critical. The balloon must have elastic properties capable of assuring an adequate seal against the vessel wall, as well as capable of allowing the struts to form the balloon into the appropriate funnel shape. The balloon material further is important since too rigid a balloon will not be formed into the funnel shape by the struts, while too weak a balloon will burst when the struts contact it.

Preferably, the outer shaft is a filled and plasticized polyvinyl chloride extrudate having a wall thickness of 0.007". Preferably the outside diameter of the shaft is between 0.054" and 0.118". The durometer of the polyvinyl chloride most preferably is Shore D86, the tensile strength is 2960 psi and the elongation at break is about 184%. Other materials that may be substituted include high density polyethylene, polypropylene or polyurethane. Of these, high density polyethylene and polypropylene have the advantage of exhibiting lower friction properties.

The flexible portion of the inner shaft also is an extrudate, preferably made from a material similar to the material of the outer shaft to facilitate heat bonding. The inner shaft must be sized to allow free relative movement between the inner shaft and outer shaft, and sized to allow for sufficient inner shaft diameter to accept the debris that will be flushed away from the brain. Thus, if the outer shaft has an outer diameter of 0.054" and an inner diameter of 0.040", then the inner shaft should have an outer diameter of not greater than 0.038". An acceptable inner diameter for the inner shaft under these circumstances is 0.030".

The inflatable balloon 16 preferably is made of a cylindrical segment of an elastomeric material such as silicon, latex or neoprene. Preferably, the inflatable balloon 16 is a medical grade silicon having a wall thickness of 0.005" and a durometer of shore A50. The balloon spans the struts 28 and is sized such that it fits snugly about the heat bonded distal end of the coaxial shafts. Thus, the balloon is slightly stretched at its opposite end proximal of the struts 28.

To manufacture applicants' occlusion component 10, the T-body 30 first is bonded to the proximal end of the outer shaft 24. Next, the outer shaft 24 is cut to the desired length (approximately 100 centimeters), and the distal end then is slit axially all the way to the distal end of the outer shaft 24 (not shown). The length of the slits is dependent on the diameter of the vessel to be occluded. Longer slits are required for larger vessels while shorter slits are required for smaller vessels. For occluding carotid arteries, a length of 18 mm has proven to be adequate. The number of slits can vary and is dependent on the material strength of the shaft. A greater number of slits provides a more circular cross-section when the funnel is formed, but the struts are not as strong. Preferably there are at least four and up to twelve slits, and most preferably six to eight appears to be ideal using the materials described above.

The flexible portion 36 of the inner shaft is bonded to a section of stainless steel hypodermic tubing, as suggested at 35. Then the distal flexible end of the inner shaft 22 is passed through the T-body 30 and outer shaft 24 until the hypodermic tubing passes into the outer shaft. The threaded cap 40 then is tightened to fix the inner and outer shafts with respect to one another. At this stage, the inner shaft 22 should extend through and beyond the distal end of the outer shaft 24. Next, the distal end of the inner shaft 22 is cut so that it extends just slightly beyond the distal end of the outer shaft 24.

After the inner shaft is cut, a teflon coated mandrel (not shown) having an outer diameter equal to the inner diameter of the inner shaft 22 is placed inside the distal end of the inner shaft 22 such that the mandrel extends at least 2 mm proximally of the distal end of the outer shaft 24. Heat and pressure are applied simultaneously to the distal end of the outer shaft 24 in a manner so as to melt the distal 2 mm onto the inner shaft 22. By using identical thermoplastic materials for the inner shaft 22 and outer shaft 24, the shafts will melt together and form a single piece at the location of the heat application. It is important that the heat be applied in a small discrete area so that only the distal 2 mm of the outer shaft 24 melts into the inner shaft 22, without further fusing of the struts together. When the heat bonding is complete, two shafts 22, 24 will be joined at their distal ends, so that retracting the inner shaft 22 proximally will cause the struts 28 at the distal end of the outer shaft 24 to buckle radially outwardly, ultimately forming the funnel shape.

The inflatable balloon 16 is bonded to the outer shaft 24 such that it spans the strutted region of the outer shaft 24. At the proximal end, the inflatable balloon 16 is bonded to a portion of the stepped region 52 of the outer shaft 24 distally just beyond the step 50 (FIGS. 3 and 4). Because it is desirable to have a smooth outer surface along the elongated shaft 14, the step 50 is sized to match the thickness of the balloon 16. Thus, the outer diameter of the outer shaft 24 proximal to the step 50 is substantially equal to the outer diameter of the elongated shaft 14 including the inflatable balloon 16 at the stepped region 52. Without the step, the inflatable balloon 16 would create an undesirable bump at its point of attachment on the outer shaft 24. The inflatable balloon 16 is attached at its distal end to the heat bonded distal end of the outer shaft 24, as suggested at 54. The slits defining the struts 28 along the frustoconical region of the outer shaft 24 allow communication between the inflation lumen 26 and the inflatable balloon 16.

The inflatable balloon 16 can be bonded onto the outer shaft 24 with any number of flexible adhesives, provided that the adhesive does not come into contact with the struts 28 underneath the inflatable balloon 16 and thus restrict their movement.

After the inflatable balloon 16 is attached to the outer shaft 24, the distal tip of the inner shaft 22 is cut off flush with the distal end of the outer shaft 24 and inflatable balloon 16. Finally, a luer connector 56 is attached to the proximal end of the rigid tubular member 38 (FIG. 2).

Figure 6A:
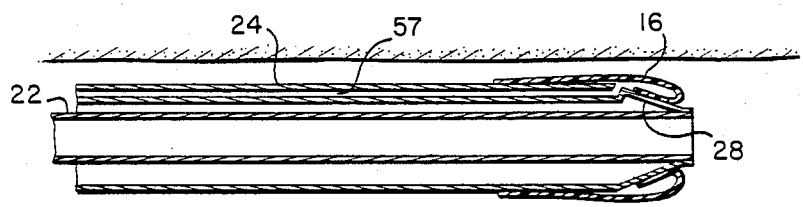
FIGS. 6A-6D are cross sectional views illustrating the operation of a second embodiment of a forming element.
Figure 6B:
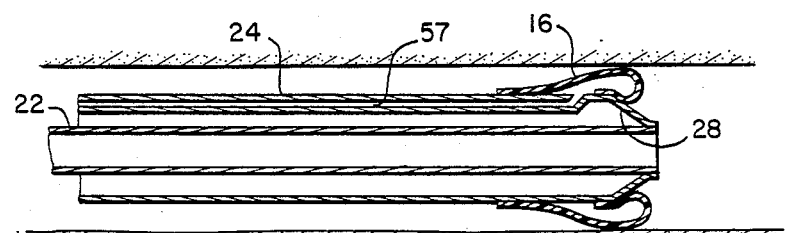
Figure 6C:
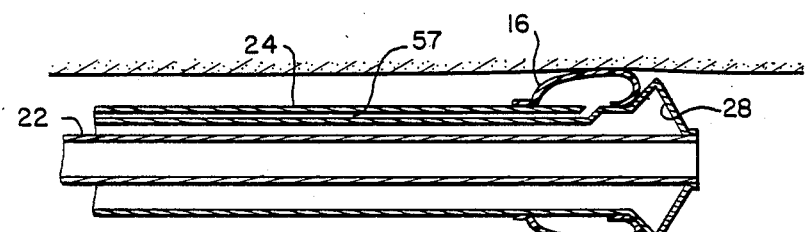

FIGS. 6A–6C show another embodiment of applicants' occlusion component 10. Like the preferred embodiment of FIGS. 3–5, the occlusion component of this embodiment includes an elongated shaft having inner and outer shafts 22 and 24, and the outer shaft 24 is provided with struts 28. Unlike the preferred embodiment, the inflatable balloon 16 is attached proximally of the struts 28, and a separate inflation lumen 57 is carried by the outer shaft 24 and communicates with the interior of the inflatable balloon 16. The annular space between the coaxial shafts 22 and 24 thus is not an inflation lumen, but rather may provide a channel for effluxing blood and debris away from the brain.

Referring to FIG. 6A, the inflatable balloon 16 is bonded at one end to a region along the outer shaft 24 proximal of the struts 28. At its other end, the inflatable balloon 16 is folded under or cuffed and bonded to the proximal end of the struts 28 with an elastic adhesive. The folded under end terminates proximally of the struts 28, and the lumen of the balloon does not communicate with the spaces between the struts.

To form the occluding element, the balloon 16 first is inflated, as shown in FIG. 6B. Then the inner shaft 22 is drawn proximally while holding the outer shaft 24 in fixed position until the struts 28 bow radially outwardly and contact the vessel wall, as shown in FIG. 6C. In this position, the portion of the struts 28 contacting the balloon shape the balloon to eliminate gutters that could entrap debris flowing proximally, and the spaces between the distal portion of the struts 28 not contacting the balloon provide efflux ports through which blood and debris may be channeled. Blood and debris also may be drawn through the open distal end of and into the lumen of the inner shaft 22.

Figure 6D:
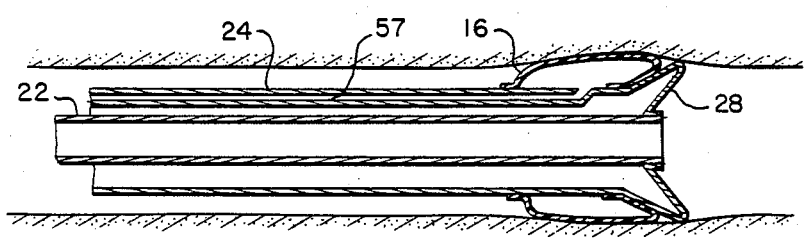

The inner shaft 22 may be drawn proximally beyond the position shown in FIG. 6C to yield a configuration similar to that shown in FIG. 5C, except that the balloon overlies the struts 28, rather than surrounding them. This position is shown in FIG. 6D.

Figure 7:
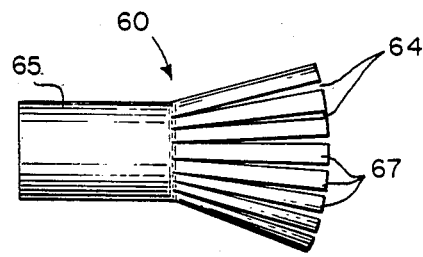
FIG. 7 is a side view of a third embodiment of a forming element.
Figure 8:
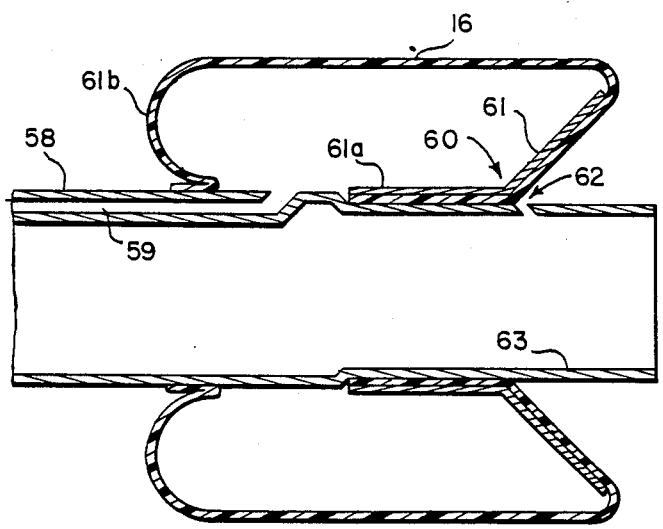
FIG. 8 is an enlarged cross-sectional view of the forming element of FIG. 7 in use with an occluding balloon and with both in their operative position.

Another embodiment of the occlusion component 10 is shown in FIG. 8 Unlike the previous embodiments, the occlusion component 10 has a single elongated shaft 58. An inflation balloon 16 is attached to the stepped, distal end of the single elongated shaft 58, which shaft carries an inflation lumen 59 communicating with the interior of the inflation balloon 16. A discrete forming element 60 shown separately in FIG. 7 is secured within the interior of the balloon 16. The forming element 60 causes the balloon when inflated to assume a funnel shape facing distally on the single elongated shaft 58. Efflux ports 62 are provided in the walls of the shaft 58 at the funnel apex 64.

The forming element 60 preferably is a short segment of a cylinder constructed of a lightweight thermoplastic material, such as polypropylene A polypropylene sold under the name Hercules Profax 6523, Hercules of Agawam, Mass., has been employed successfully. One end of the forming element is slit axially and splayed over a conical mold to produce a funnel-shaped splayed end 64. The opposite end 65 is left as a cylinder.

To construct the occlusion component of this embodiment, one end 61 of the elastic balloon 16 corresponding in length to the forming element 60 is slipped over the distal end 63 of the shaft 58. The leading portion 61a of this end, which is to underlie the cylindrical end 65 of the forming element 60, is bonded to the shaft. Then, the forming element 60 is threaded over the portion of the balloon 16 extending from the shaft and onto the shaft until the cylindrical end 65 of the forming element 60 overlies the portion 61a of the balloon 16 bonded to the shaft. The cylindrical end 65 and the individual splays 67 of the forming element are then bonded to the balloon. A convenient way to bond the individual splays 67 to the balloon 16 is to apply an elastic adhesive to the underside of the splays 67 and then to hold the splays 67 against the balloon 16 while the adhesive cures, by, slipping a tube over splays 67. Finally, the opposite end 61b of the balloon 16 is folded back upon itself and over the forming element, and then conventionally secured to the shaft at a point proximal to the forming element.

Inflation of the elastic balloon 16 causes the forming element 60 to assume its funnel shape, thus forcing the balloon 16 into the desired configuration. The elasticity of the balloon 16 will return the forming element 60 to a cylindrical shape upon deflation of the balloon, which facilitates passage of the device into and out of the vessels.

The preferred method according to this invention is illustrated in FIGS. 9A-9F, wherein a cerebral vessel 66 is suggested having a stenosis 70. The lumen of the cerebral vessel 66 is accessed in one of three ways, depending on the location of the stenosis. Lesions in the distal posterior circulation would be approached by a cut down to the vertebral artery. Lesions in the distal anterior circulation would be approached percutaneously through the common carotid arteries. Proximal lesions in all vessels would be approached percutaneously through the femoral artery In each case, after the vasculature is accessed, a conventional guidewire 68 is passed within the lumen of the cerebral vessel 66 and across the lesion 70 to be dilated (FIG. 9A). Next, the occlusion component 10 is introduced over the guidewire into the cerebral vessel 66, stopping proximal of the lesion 70 (FIG. 9B). Next, the therapeutic device of choice is introduced through the lumen of the inner shaft 22 and over the guidewire 68 to access the lesion 70 (FIG. 9C). Then, the occluding element of the occlusion component 10 is activated If either of the devices having coaxial shafts is used, then the occlusion balloon 71 first is inflated until the vessel is fully occluded. This can be determined by fluoroscopic visualization of the stagnant flow created by the occlusion, or by gentle traction on the catheter. Once occlusion is confirmed, the inner shaft 22 is displaced proximally while holding the outer shaft 24 fixed, resulting in the formation of the funnel shaped occluding element 73 as shown in FIG. 9D. Once the occluding element is formed, treatment of the lesion 70 is initiated. For example, the intervention component may be a balloon dilitation catheter 72 and treatment may consist of inflating the dilitation balloon 74 at the site of the lesion 70. When the dilitation is complete, the dilitation balloon 74 is deflated and the retrograde blood flow represented by the arrows 77 in FIG. 9E will flush the blood and debris in the funnel 73 and through the lumen of the inner shaft for several seconds. After this flushing step, the inner shaft 22 is moved distally to cause the struts to lie flat and the inflatable occlusion balloon 71 is deflated to reestablish antegrade flow (arrows 79 in FIG. 9F). This pattern repeated until satisfactory treatment of the lesion is accomplished. Finally, the device is removed.

Figure 10A:
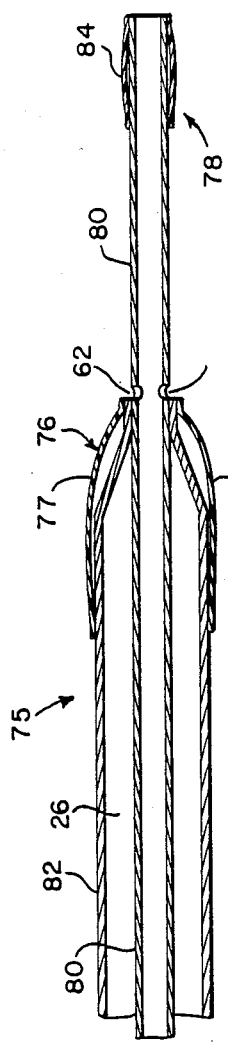
FIGS. 10A-B are cross sectional views of another embodiment of the angioplasty system in accordance with this invention.
Figure 10B:
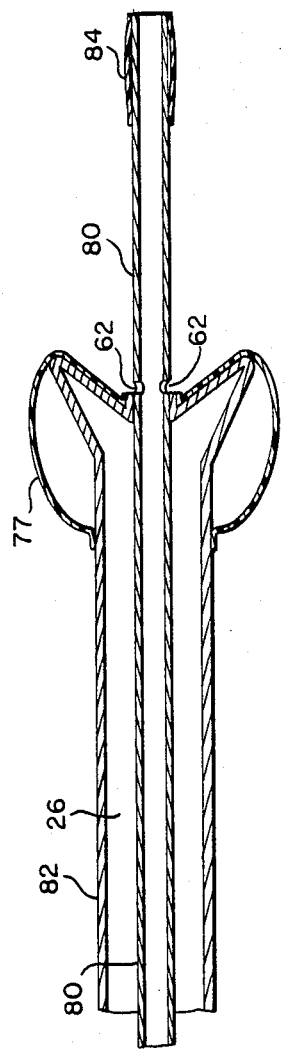

FIGS. 10A-10B show yet another embodiment of the invention. In this embodiment, the occlusion component and intervention component are not separate elements but rather are features of a unitary device. An elongated shaft 75, sized to be introduced into a blood vessel, carries on its distal end both an occlusion element 76 and an intervention element 78. The occlusion element 76 is located several centimeters proximally of the intervention element. The occlusion element includes an occlusion balloon 77 and is capable of being formed into a distally-facing funnel in the blood vessel.

The elongated shaft 75 is composed of coaxial inner and outer shafts 80 and 82, respectively. The distal end of the inner shaft 80 extends several centimeters beyond the distal end of the outer shaft 82, the distal end of the outer shaft 82 being operatively connected to the inner shaft 80. The annular space between the shafts defines an inflation lumen 26 which communicates with the interior of the occlusion balloon 77. The occlusion balloon 77 is attached at the distal end of the outer shaft 80. Efflux ports 62 are located at the apex of the funnel that is formed by the occlusion balloon 77 when inflated, as illustrated in FIG. 10A. The intervention element is a dilitation balloon 84 attached to the distal end of the inner shaft 80 and communicating with an inflation lumen (not shown) carried along the inner shaft 80.

To form the occlusion component, the outer shaft's distal end is slit axially (not shown) for about 18 mm and the terminal 2 mm of this slit distal end is heat bonded to the inner shaft 80 several centimeters from the distal end of the inner shaft 80. The heat bonding melts the distal end of the outer shaft 82 to the inner shaft 80 and eliminates the slits at the heat bonded area. The unmelted portion of the slits defines a cylindrical series of struts (not shown), as described in connection with FIG. 4. The occlusion balloon 77 completely spans the struts. The interior of the occlusion balloon communicates with the annular inflation lumen 26 through the slits.

The proximal end of the device is constructed the same as the proximal end of the preferred embodiment, described above in connection with FIG. 2. The proximal end of the outer shaft is attached to a T-body (not shown) and the proximal end of the inner shaft is a rigid member (not shown) that extends completely through the T-body. The T-body and T-body cap (not shown) seal the proximal end of the inflation lumen and at the same time allow for the axial movement of the inner shaft. As described above in connection with FIGS. 5A-C, the balloon may be inflated, and the inner shaft may be moved proximally while holding the outer shaft fixed to cause the struts to form the balloon into a distally facing funnel, as shown in FIG. 10B.

It should be understood that other embodiments of an occlusion element may be substituted for the embodiment described in connection with FIGS. 10A and 10B. For example, the occlusion components described in connection with FIGS. 6-8 may be used.

The device of FIGS. 10A and 10B is used as shown in FIGS. 11A-11E. As in the method of FIGS. 9A-9F, a guidewire 68 is introduced into the lumen of the vessel 66 and extends across the lesion 70, as shown in FIG. 11A. Next, the device of FIGS. 10A and 10B is introduced over the wire and advanced until the dilitation balloon 84 is located at the stenosis, with the occlusion balloon 77 being located several centimeters proximal of the stenosis, as illustrated in FIG. 11B. Then, the occlusion balloon 77 is inflated to occlude the vessel and the inner shaft 80 is withdrawn proximally to shape the occlusion balloon 77 into a distally-facing funnel (11C). Next, the dilitation balloon 84 is inflated to treat the lesion 70 (11D), and then the dilitation balloon 84 is deflated. Deflation of the dilitation balloon 84 is accompanied by retrograde flushing (arrow) of the blood and debris from the treated lesion through the efflux ports 62 and into the lumen of the device (FIG. 11E). Finally, the inner shaft is moved distally to flatten the struts; the occlusion balloon 77 is deflated; and the device is removed.

It should be understood that various changes and modifications of the embodiments shown in the drawings and described above may be made within the scope of this invention. For example, while elastic balloons and thermoplastic forming elements are described for forming a funnel shaped occlusion element, other configurations are both possible and contemplated. It is only necessary that the occlusion element be capable of occluding the vessel to establish retrograde flow of blood and to be capable of providing for the collection of debris in a manner that does not permit the debris to become entrapped in annular gutters formed by the occlusion device. To avoid entrapping debris, the occlusion element should define surfaces that efficiently channel blood and debris contacting those surfaces continuously in a proximal direction to efflux ports, the efflux ports being located at the proximal end of the channeling surfaces. To accomplish this, distally funnel shaped, inflatable occluding elements have been described. In two of the embodiments described (FIGS. 5C and 8), the periphery of the occluding device meets the walls of the vessel at an oblique angle and with a smooth transition so that debris will not become entrapped at the funnel-vessel wall interface. Efflux ports are located at the base or apex of the funnel. In another embodiment, shown in FIG. 6C, peripheral efflux ports (the slits) are provided at the vessel-wall occlusion device interface and fluid and debris are channeled to and exit via these peripheral efflux ports. Also, while the intervention component shown in the preferred embodiment is a dilitation balloon, the intervention component may be any therapeutic device that treats debris such as a catheter capable of introducing a chemical, a laser ablation catheter, a thermal probe, an arthrectomy catheter, or a prosthetic stent.

It is intended that all matter contained in the above description or shown in the accompanying drawings shall be interpreted in an illustrative and not limiting sense.

What is claimed is:

1. A blood vessel occlusion catheter for use during therapeutic intervention of a blood vessel for flushing away fluid and debris from the area of the therapeutic intervention comprising,
    an elongated shaft sized to be introduced into the blood vessel lumen,
    occlusion means secured to the shaft at or near the distal end of the shaft, the occlusion means capable of forming a funnel with the larger end of the funnel facing distally on the shaft and contacting the vessel walls to form a seal against the vessel walls,
    an inflation lumen carried by the shaft and communicating with the interior of the occlusion means enabling the occlusion means to be inflated into the shape of said funnel, wherein the occlusion means when inflated defines surfaces capable of channeling all fluid and debris contacting the surfaces continuously in a proximal direction to an efflux means,
    efflux means enabling fluid and debris to be carried within the shaft toward and out of the proximal end of the shaft, and
    intervention means located on the shaft distal to the inflatable means for treating a site along the blood vessel.

2. An occlusion catheter for use during therapeutic intervention of a blood vessel for flushing away fluid and debris from the area of the therapeutic intervention comprising,
    an elongated shaft sized to be introduced into the blood vessel lumen,
    occlusion means secured to the shaft at or near the distal end of the shaft, the occlusion means capable of forming a funnel with the larger end of the funnel facing distally on the shaft and contacting the vessel walls to form a seal against the vessel walls, wherein said inflatable occlusion means comprises an elastic balloon secured to the shaft,
    an inflation lumen carried by the shaft and communicating with the interior of the occlusion means enabling the occlusion means to be inflated into the shape of said funnel, wherein the occlusion means when inflated defines surfaces capable of channeling all fluid and debris contacting the surfaces continuously and at a proximal direction to an efflux means,
    efflux means enabling fluid and debris to be carried within the shaft toward and out of the proximal end of the shaft, and
    means located on the shaft and radially extending therefrom for engaging the balloon for causing the distal end of the balloon to form a funnel, the larger end of said funnel capable of forming a seal against the vessel walls.

3. A blood vessel occlusion catheter for use during therapeutic intervention of a blood vessel for flushing away fluid and debris from the area of the therapeutic intervention comprising,
    an elongated shaft sized to be introduced into the blood vessel lumen,
    an elastic balloon secured to the shaft at or near its distal end,
    an inflation lumen carried by the shaft and communicating with the interior of the balloon enabling the balloon to be inflated and for causing it to form a seal against the vessel proximally of the therapeutic intervention,
    means attached to the shaft and radially extending therefrom for engaging the balloon for causing the distal end of the balloon to form a funnel with the larger end of the funnel facing distally on the shaft when the balloon is inflated,
    and efflux means at the base of the funnel enabling fluid and debris which enter the funnel to be carried within the shaft toward and out of its proximal end.

4. An occlusion catheter as defined in claim 3 further comprising,
    intervention means located on the shaft distal to the elastic balloon for treating a site along the blood vessel.

5. An occlusion catheter as defined in claim 3 wherein a second lumen is carried by the shaft, the second lumen having a sufficient diameter such that a dilitation catheter or other therapeutic device may be passed through the second lumen.

6. An occlusion catheter as defined in claim 3 wherein a second shaft extends through the first recited shaft and communicates with the efflux means to carrying the fluid and debris.

7. An occlusion catheter as defined in claim 6 wherein the means engaging the balloon includes the first shaft, said second shaft being movable axially with respect to the first shaft to cause the first shaft to form the balloon into a funnel.

8. An occlusion catheter as defined in claim 7 wherein a second lumen is carried by the second shaft, the second lumen having a sufficient diameter such that a dilitation catheter or other therapeutic device may be passed through the second lumen.

9. An occlusion catheter as defined in claim 7 wherein the second shaft extends distally of the first shaft and further comprising,
intervention means carried on the second shaft distal of the elastic balloon for treating a site along the blood vessel.

10. An occlusion catheter as defined in claim 9 wherein the intervention means is a dilitation balloon secured to the second shaft and communicating with a second inflation lumen carried by the second shaft and enabling the dilitation balloon to be inflated at the site of the therapeutic intervention.

11. An occlusion catheter as defined in claim 6 wherein the two shafts form an annular lumen between them which comprises the inflation lumen.

12. An occlusion catheter for use during therapeutic intervention of a blood vessel for flushing away fluid and debris from the area of the therapeutic intervention comprising,
an elongated shaft sized to be introduced into the blood vessel lumen,
an elastic balloon secured to the shaft at or near its distal end,
an inflation lumen carried by the shaft and communicating with the interior of the balloon enabling the balloon to be inflated and for causing it to form a seal against the vessel proximally of the therapeutic intervention,
means engaging the balloon for causing the distal end of the balloon to form a funnel with the larger end of the funnel facing distally on the shaft when the balloon is inflated, said means engaging the balloon including a plurality of struts on the shaft extending in an axial direction with respect to the shaft,
additional means connected to the struts for moving the distal end and proximal ends of the struts toward one another and moving the intermediate portions of the struts radially outward to form the funnel in the distal end of the balloon, and
efflux means at the base of the funnel enabling fluid and debris which enter the funnel to be carried within the shaft to its proximal end.

13. An occlusion catheter as defined in claim 12 wherein
the additional means includes a second shaft extending in an axial direction in the first recited shaft and connected to one end of the struts.

14. An occlusion catheter as defined in claim 13 wherein
the second shaft is connected to the distal ends of the struts and is movable axially in the first recited shaft.

15. An occlusion catheter as defined in claim 14 wherein
the second shaft is coaxial with the first recited shaft and the distal end of the first recited shaft is connected to the second shaft,
and axially extending slits in the distal end of the first recited shaft closely adjacent the connection between the shafts define the struts within the balloon.

16. An occlusion catheter as defined in claim 15 wherein
the slit distal end of the first-recited shaft tapers in a distal direction to the surface of the second shaft.

17. An occlusion catheter as defined in claim 15 wherein a second lumen is carried by the second shaft, the second lumen having a sufficient diameter such that a dilitation catheter or other therapeutic device may be passed through the second lumen.

18. An occlusion catheter as defined in claim 17 wherein the second shaft extends distally of the first shaft and further comprising,
intervention means carried on the second shaft distal to the elastic balloon means for treating a site along the blood vessel.

19. An occlusion catheter as defined in claim 18 wherein the intervention means is a dilitation balloon secured to the second shaft and communicating with a second inflation lumen carried by the second shaft and enabling the dilitation balloon to be inflated at the site of the therapeutic intervention.

20. An occlusion catheter as defined in claim 15 wherein the two shafts form an annular lumen between them which comprises the inflation lumen.

21. An occlusion catheter for use during therapeutic intervention of a blood vessel for flushing away fluid and debris from the area of the therapeutic intervention comprising,
an elongated shaft sized to be introduced into the blood vessel lumen,
an elastic balloon secured to the shaft at or near its distal end,
an inflation lumen carried by the shaft and communicating with the interior of the balloon enabling the balloon to be inflated and for causing it to form a seal against the vessel proximally of the therapeutic intervention,
means engaging the balloon for causing the distal end of the balloon to form a funnel with the larger end of the funnel facing distally on the shaft when the balloon is inflated, comprising a cylindrical element secured to the shaft and within the balloon and splayed at its distal end to form the funnel facing in a distal direction when the balloon is inflated and,
efflux means at the base of the funnel enabling fluid and debris which enter the funnel to be carried within the shaft to its proximal end.

22. An occlusion catheter as defined in claim wherein splayed end of the cylindrical element comprises a series of struts, said struts collapsing against the surface of the shaft when the balloon is deflated and splaying outwardly from the shaft when the balloon is inflated.

23. An occlusion catheter as defined in claim 22 further comprising,
intervention means carried on the shaft distal to the elastic balloon for treating a site along the blood vessel.

24. An occlusion catheter as defined in claim 23 wherein the intervention means is a dilitation balloon secured to the shaft and communicating with a second inflation lumen carried by the shaft and enabling the dilitation balloon to be inflated at the site of the therapeutic intervention.

25. An occlusion catheter as defined in claim 22 wherein a second lumen is carried by the shaft, the second lumen having a sufficient diameter such that a dilitation catheter may be passed through the second lumen.

26. An occlusion catheter for use during therapeutic intervention of a blood vessel for flushing away fluid and debris from the brain comprising,
   a multi lumen elongated shaft sized to be introduced into the blood vessel lumen,
   a forming element disposed over the distal end of the shaft and connected at its proximal end to the shaft, the distal end of the element being slit and splayed in a distal direction,
   an elastic balloon secured at its proximal end to the shaft proximally of the splayed end of the element, and secured at its distal end to the shaft in a manner to encircle the splayed end of the element,
   means connecting the interior of the balloon to one of the lumens of the shaft so that the balloon can be inflated and form a seal against the wall of the vessel lumen,
   said splayed end of the element assuming a funnel shape with its larger end facing distally when the balloon is inflated and causing the balloon to conform to the shape of the funnel, and said element collapsing against the outer surface of the shaft when the balloon is deflated,
   and means connecting the apex of the funnel with another of the lumens of the shaft so that the retrograde flow from the site of intervention will enter the funnel and be carried toward the proximal end of the shaft.

27. A catheter system for transluminal angioplasty of the cerebral vessels comprising,
   an elongated multilumen shaft means sized to be introduced into the vessel lumen,
   inflatable means secured to the shaft means near its distal end, the inflatable means capable of forming a funnel with the larger end of the funnel facing distally on the shaft means when inflated,
   an inflation lumen passing axially through the shaft means and communicating with the interior of the inflatable means enabling the inflatable means to be inflated and causing it to form a funnel, the larger end of which forms an occluding seal against the vessel walls, efflux means at the base of the funnel communicating with an efflux lumen passing axially through the shaft means enabling fluid and debris which enter the funnel to be carried into the shaft toward its proximal end,
   an intervention lumen extending axially through the shaft means,
   and intervention means capable of being delivered through the intervention lumen to a site in the vessel distal to the inflatable means for therapeutically treating the site,
   wherein the inflatable means comprises a balloon and a plurality of struts engaging the balloon, the struts extending in an axial direction with respect to a first shaft of the shaft means, and a second shaft of said shaft means extending axially and movable in the first shaft and connected to the distal ends of the struts for moving the distal and proximal ends of the struts closer to one another and moving the intermediate portions of the struts radially outward toward the wall of the vessel lumen to form the distal end of the balloon into a funnel shape.

28. A catheter system for transluminal angioplasty as claimed in claim 27 wherein the annular space between the shaft means defines the inflation lumen which communicates with the inside of the balloon through spaces between the struts.

29. A catheter system for transluminal angioplasty as claimed in claim 28 wherein the second shaft is tubular and the lumen of the second shaft defines the intervention lumen.

30. A catheter system as defined in claim 29 wherein the intervention means is a balloon dilitation catheter.

31. A catheter system as defined in claim 7 wherein the inflatable means comprises a balloon and a balloon-forming element and, wherein the balloon-forming element comprises a cylindrical element secured to the shaft within the balloon and splayed its distal end to form the funnel facing in a distal direction when the balloon is inflated.

32. A catheter system as defined in claim 31 wherein the splayed end collapses against the surface of the shaft when the balloon is deflated and splays outwardly from the shaft when the balloon is inflated.

33. A catheter system as defined in claim 32 wherein the intervention means is a balloon dilitation catheter.

34. A method for therapeutic intervention at a site in a cerebral vessel comprising,
   occluding the cerebral vessel at a location proximal and close to the intervention site to establish retrograde flow in said vessel distal of said occlusion,
   therapeutically treating the intervention site,
   collecting and withdrawing from the vessel fluid and debris moved to the occlusion by the retrograde flow, and
   reestablishing antegrade flow of blood through the vessel.

35. A method for therapeutic intervention as defined in claim 34 wherein the cerebral vessel is occluded by forming a funnel shaped occlusion seal, the larger end of the funnel facing distally in the vessel and contacting the vessel to form the seal.

36. A method for therapeutic intervention as defined in claim 35 characterized by collecting the retrograde flowing fluid and debris in the funnel and allowing the fluid and debris to be flushed from the vessel through ports at the base of the funnel.

37. A method for therapeutic treatment as defined in claim 36 wherein the funnel shaped occlusion seal is formed by inflating an elastic balloon carried on the shaft.

38. A method for therapeutic treatment as defined in claim 37 wherein the shaft has a lumen and the intervention site is treated by introducing a balloon dilitation catheter distally through the lumen until the balloon lies across the treatment site and then inflating the balloon.

39. A method for therapeutic intervention at a site in a cerebral vessel comprising,
   introducing an occluding means and a treatment means into a cerebral vessel, the occluding means carried on a shaft having efflux means capable of acting with the occluding means to collect and withdraw from the vessel fluid and debris distal of the occluding means,
   activating the occluding means to seal the vessel at a location proximal of the intervention site and to establish retrograde flow in the vessel distal of the occluding seal,
   therapeutically treating the intervention site with the treatment means,
   collecting and withdrawing fluid and debris distal of the occluding seal through the efflux means, the retrograde flow moving debris toward the efflux means, and deactivating the occlusion means to reestablish antegrade flow in the vessel.

40. A method for therapeutic intervention as defined in claim 39 wherein the occluding means is a balloon, an inflation lumen and balloon forming elements, all carried on the shaft, and further comprising the steps of inflating the balloon via the inflation lumen and causing the forming elements to act upon the balloon to form a funnel shaped occlusion seal, the larger end of the funnel facing distally and contacting the vessel to seal the vessel.

41. A method for therapeutic intervention as defined in claim 40 wherein the therapeutic treatment comprises inflating a dilitation balloon at the intervention site.

42. A method for therapeutic treatment as defined in claim 41 wherein the shaft has a second lumen and the treatment further comprises advancing a balloon dilitation catheter distally through the second lumen until the dilitation balloon lies across the treatment site.

43. A method for therapeutic intervention as defined in claim 41 wherein the treatment means is carried on the same shaft as the occlusion means and the shaft is introduced into the cerebral vessel and advanced until the treatment means is located at the treatment site.

44. A method for therapeutic treatment as defined in claim 43 wherein the occlusion means includes an occlusion balloon and the treatment means is a dilitation balloon, and wherein the occluding means is activated by inflating the occlusion balloon and causing it to form a distally facing funnel shaped seal and the treatment comprises inflating the dilitation balloon.

45. A method for therapeutic intervention as defined in claim 44 wherein the efflux means includes efflux ports located at the base of the funnel shaped occluding seal and further comprising collecting the fluid and debris flowing retrograde from the intervention site in the funnel and withdrawing the fluid and debris from the vessel through the efflux ports.

* * * * *